United States Patent [19]

Hung

[11] Patent Number: 5,196,569
[45] Date of Patent: Mar. 23, 1993

[54] FUNCTIONALIZED TRIFLUOROVINYL ETHERS AND POLYMERS THEREFROM

[75] Inventor: Ming-Hong Hung, Wilmington, Del.

[73] Assignee: E. I. Du Pont de Nemours and Company, Wilmington, Del.

[21] Appl. No.: 774,407

[22] Filed: Oct. 10, 1991

Related U.S. Application Data

[63] Continuation-in-part of Ser. No. 532,618, Jun. 4, 1990, abandoned.

[51] Int. Cl.$^5$ .................. C07C 69/52; C07C 21/02; C07C 43/14; C07D 303/12
[52] U.S. Cl. ..................... 560/223; 549/554; 549/558; 564/442; 568/606; 568/607; 568/608; 568/615; 568/630; 568/662; 568/663; 568/669; 568/670; 568/674; 526/247
[58] Field of Search ............... 568/615, 674, 606, 669, 568/670, 607, 662, 663, 608, 630; 549/554, 558; 560/223; 564/442

[56] References Cited

U.S. PATENT DOCUMENTS

| 4,544,720 | 10/1985 | Ohmori et al. | 526/247 |
| 4,556,747 | 12/1985 | Resnick | 568/674 |
| 4,564,717 | 1/1986 | Chmori et al. | 568/843 |
| 4,982,009 | 1/1991 | Hung | 568/615 |

FOREIGN PATENT DOCUMENTS 199138 10/1986 European Pat. Off.
88-002418 1/1988 Japan.

*Primary Examiner*—marianne M. Cintins
*Assistant Examiner*—Rebecca Cook
*Attorney, Agent, or Firm*—Nancy S. Mayer

[57] ABSTRACT

Trifluorovinyl ethers containing selected functional groups, and homo- and copolymers prepared from them, are disclosed, as well as intermediates useful in the preparation of the ethers.

9 Claims, No Drawings

FUNCTIONALIZED TRIFLUOROVINYL ETHERS AND POLYMERS THEREFROM

CROSS-REFERENCE TO RELATED APPLICATION

This application is a continuation-in-part of copending U.S. patent application Ser. No. 07/532,618 filed Jun. 4, 1990, now abandoned.

FIELD OF INVENTION

This invention concerns selected trifluorovinyl ethers containing various functional groups, and polymers prepared from them by free radical polymerization. Also provided are intermediates for use in the preparation of the trifluorovinyl ethers.

BACKGROUND OF THE INVENTION

Japanese Patent 88002418 reports the synthesis of 7,7-dihydro-7-hydroxy(perfluoro-3-oxahepten-1) by chlorinating the methyl ester of perfluoro(3-oxa-1-heptenoic acid), reduction of the chlorinated product with $NaBH_4$ to give the corresponding alcohol, and then reaction of the alcohol with zinc metal to regenerate the vinyl ether, which is the desired product. It is reported that this compound can be free radically copolymerized with at least one other fluorinated monomer, and optionally non-fluorinated monomers to form useful polymers.

U.S. Pat. No. 4,564,717 reports the synthesis of compounds of the formula $CF_2=CF(CF_2)_m(CH_2)_nOH$ wherein m is an integer from 0 to 10 and n is an integer of 1 to 4. Among the methods of preparation described, is the reduction of the compound $CF_2X^1CFX^2CF_2COOR$ (sic) wherein R is alkyl and $X^1$ and $X^2$ are chlorine or bromine, by various reducing agents. The olefin is then produced by dehalogenation of the alcohol with a metal such as zinc.

European Patent Application 135,917 discloses copolymers of vinylidene fluoride with a compound of the formula $CF_2=CF(CF_2)_m(CH_2)_nOH$ wherein m is 0 to 10 and n is 1–4, and optionally another fluorinated termonomer. Polymers containing fluorovinyl ethers are not disclosed.

European Patent Application 199,138 reports preparation and polymerization (with other fluorine containing olefins) of the compound $CF_2=CFO(CF_2CFYO)_n(CF_2CF_2CH_2O)_mCF_2CF_2CH_2X$, wherein X is hydrogen or halogen, Y is fluorine or $-CF_3$, m is an integer of 0 to 5 and n is 0, 1 or 2. No mention is made of other functional groups being present.

It is the object of this invention to provide trifluorovinyl ether monomers that contain various functional groups. The functional groups may be chemically relatively inert, such as alkyl ether, which when used in a minor proportion in a fluorinated polymer, changes the surfaces properties of that polymer. The functional group may also be more chemically active, such as epoxy, which may be utilized as a crosslinking or adhesion promotion site. Finally the functional group may be styryl or acrylic so that the functional group may be readily polymerized. Also provided are the homo- and copolymers of such compounds, and intermediate compounds from which such trifluorovinyl ethers are made.

SUMMARY OF THE INVENTION

This invention comprises a trifluorovinyl ether of the formula I

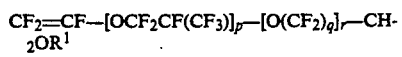      I wherein:
$R^1$ is alkyl or cycloalkyl containing 1 to 30 carbon atoms,

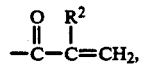

$-(CH_2)_sR^3$ or $-(CH_2)_tR^5$;
$R^2$ is hydrogen or methyl;
$R^3$ is $-C\equiv CH$, $-CH=CH_2$, styryl or

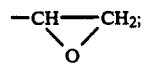

$R^5$ is aryl or substituted aryl;
p is an integer of 0 to 20;
q is an integer of 1 to 10;
r is 0 or 1;
s is 1, 2, 3 or 4; and
t is 0, 1, 2, 3 or 4;
provided that when r is 0, p is not 0.

A further aspect of this invention comprises halogenated compounds of the formula II

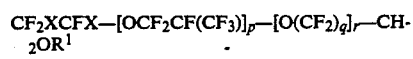      II wherein:
$R^1$ is alkyl or cycloalkyl containing 1 to 30 carbon atoms,

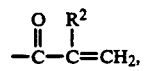

$-(CH_2)_sR^3$, $-(CH_2)_tR^5$ or hydrogen;
$R^2$ is hydrogen or methyl;
$R^3$ is $-C\equiv CH$, $-CH=CH_2$, styryl or

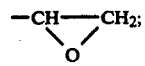

$R^5$ is aryl, or substituted aryl;
each X is independently chlorine or bromine;
p is an integer of 0 to 20;
q is an integer of 1 to 10;
r is 0 or 1;
s is 1, 2, 3 or 4; and
t is 0, 1, 2, 3, or 4;
provided that when r is 0, p is not 0, and further provided that when p is 0, q is three, r is 1, and $R^1$ is not hydrogen.

A further aspect of this invention comprises copolymers of trifluorovinyl ethers comprising units of the formula III

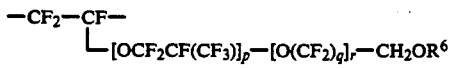

III and one or more free radically polymerizable monomer
wherein:
R$^6$ is alkyl or cycloalkyl containing 1 to 30 carbon atoms, —(CH$_2$)$_s$R$^8$, or —(CH$_2$)$_t$R$^5$;
R$^8$ is —C≡CH, —CH=CH$_2$, or

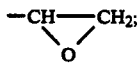

R$^5$ is aryl, and substituted aryl;
p is an integer of 0 to 20;
q is an integer of 1 to 10;
r is 0 or 1;
s is 1, 2, 3 or 4; and
t is 0, 1, 2, 3, or 4;
provided that when r is 0, p is not 0.

Also provided is a polymer made by the free radical polymerization of a compound of the formula IV

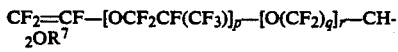

IV and optionally other vinyl monomers, wherein:
R$^7$ is

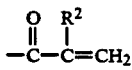

or —(CH$_2$)$_s$R$^4$;
R$^2$ is hydrogen or methyl;
R$^4$ is styryl;
p is an integer of 0 to 20;
q is an integer of 1 to 10;
r is 0 or 1; and
s is 1, 2, 3 or 4;
provided that when r is 0, p is not 0.

DETAILS OF THE INVENTION

The term "styryl" is used herein to mean the group o-, m-, or p-vinylphenyl, which may have inert substituents bound to the benzene ring.

By the term "substituted aryl" herein is meant an aryl group substituted with any group that does not interfere with, and is stable during, any of the reactions the particular compound containing that group has or will undergo. Examples of suitable substituents include, but are not limited to, halo, ester alkyl, ether, aryl, nitro, cyano and cyloalkyl.

The trifluorovinyl ethers of this invention may be prepared from the halogenated compounds of this invention, which in turn are made by known processes from known starting materials. Thus the halogenated compound of formula II wherein both Xs are chlorine, p is 1, q is 2, r is 1 and R$^1$ is hydrogen is made by the chlorination of CF$_2$=CFOCF$_2$CF(CF$_3$)OCF$_2$CF$_2$COOCH$_3$. See U.S. Pat. No. 4,138,426, which is herein incorporated by reference, for preparation of this compound, and subsequent reduction of the methyl ester to the alcohol (see Example 1). This alcohol, and others such as those described in Japanese Patent 88002418, can then be converted to ethers or esters using the reactions described herein. That is, R$^1$ is changed from hydrogen to one of the other groups listed for R$^1$ supra, in the formula of the halogenated compound.

Ethers may be made by variations of the Williamson ether synthesis, a reaction well known to those skilled in the art. Briefly, an alcohol is converted to its alkoxide, and the alkoxide is reacted with a (cyclo)alkyl halide to yield the corresponding ether. The alkyl halide may be substituted with various functional groups, so long as these group do not react with the alkoxide faster than the halide does. Such reactions are illustrated in Examples 2-7 herein. A general reference on such reactions is H. Feuer and J. Hooz in S. Patai, Ed., The Chemistry of the Ether Linkage, Interscience Publishers, London, 1967, p. 446-448.

The halogenated compounds in which R$^1$ is hydrogen (that is halogenated compound "alcohols") may be converted to their corresponding acrylic esters by standard esterification reactions. For example the alcohol may be reacted with an acrylyl or methacrylyl halide, preferably the chloride, to form the (meth)acrylic ester. Such reactions, and others useful for esterification, are well known to those skilled in the art.

In preferred embodiments of the halogenated compounds of formula II, p is 0, r is 1 and q is 1 to 10; or p is 1, r is 1 and q is 2. In another preferred embodiment of the halogenated compound both groups X are chlorine. Preferred groups R$^1$ are: n-alkyl; —(CH$_2$)$_s$R$^3$ wherein s is 1 and R$^3$ is —C≡CH, —CH=CH$_2$ or styryl; or —(CH$_2$)$_t$R$^5$ wherein t is 0 or 1. Especially preferred R$^1$ groups are (CH$_2$)$_s$R$^3$ wherein s is 1 and R$^3$ is —CH=CH$_2$ or styryl. It is also preferred that when t is 0, the group R$^5$ be substituted with, or have substituents derived from, electron withdrawing groups, such as nitro or cyano. Amino, for example, is a substituent derived from an electron withdrawing group, namely nitro. Also preferred are any and all combinations of the above preferred embodiments.

Preferred specific halogenated compounds are:

3,6,10-trioxa-1,2-dichloro-1,1,2,4,4,5,7,7,8,8-decafluoro-5-trifluoromethyl-12,13-epoxytridecane;
3,6,10-trioxa-1,2-dichloro-1,1,2,4,4,5,7,7,8,8-decafluoro-5-trifluoromethylhexadecane;
3,6,10-trioxa-1,2-dichloro-1,1,2,4,4,5,7,7,8,8-decafluoro-5-trifluoromethyloctacosane;
4,8,11-trioxa-12,13-dichloro-6,6,7,7,9,10,10,12,13,13-decafluoro-9-trifluoromethyltridec-1-yne;
3,6,10-trioxa-1,2-dichloro-1,1,2,4,4,5,7,7,8,8-decafluoro-5-trifluoromethyl-11—(vinylphenyl)undecane;
(3,6,10-trioxa-1,2-dichloro-1,1,2,4,4,5,7,7,8,8-decafluoro-5-trifluoromethylnonyl) 2,4-dinitrophenyl ether; and
(3,6,10-trioxa-1,2-dichloro-1,1,2,4,4,5,7,7,8,8-decafluoro-5-trifluoromethylnonyl) 2,4-diaminophenyl ether.

The trifluorovinyl ethers of formula I of the present invention may be prepared by the dehalogenation of the above described halogenated compounds, by direct reaction of the corresponding trifluorovinyl ether alcohol, or by reaction of the group R$^1$ of a trifluorovinyl ether to form a different R$^1$ group. The latter two methods are preferred if the final group on the trifluorovinyl ether is relatively reactive, especially in a dehalogenation reaction.

The dehalogenation of 1,2-dichloro- or 1,2-dibromotrifluoroethoxy groups with an active metal such as zinc to form trifluorovinyl ether groups is known to those skilled in the art, for example see Japanese Patent 88002418 and U.S. Pat. No. 4,564,717, supra. This reaction is illustrated in Examples 9–12 herein. The groups $R^1$ should be stable to the reaction conditions.

The reaction of the corresponding trifluorovinyl ether alcohol to form a trifluorovinyl ether claimed herein is particularly useful where a functional group that may be reactive in the dehalogenation reaction is desired. Such a reaction is the esterification of the alcohol to form an acrylic ester. For example, the alcohol may be reacted with a (meth)acrylyl halide, preferably the chloride, to form a (meth)acrylic ester. This and similar esterification reactions are known to those skilled in the art. Example 13 herein illustrates such a reaction.

Finally certain of the trifluorovinyl ethers claimed herein may be made by reaction of a functional group within $R^1$ to form a different functional group. This reaction is also particularly useful when the final functional group may not be stable to the dehalogenation reaction. An example of such a reaction is the epoxidation of a vinyl group to an epoxide. For example, when $R^1$ is $-(CH_2)_sR^3$, and $R^3$ is $-CH=CH_2$, the vinyl group may be oxidized by typical epoxidation reactions (for example see Kirk-Othmer Encyclopedia of Chemical Technology, 3rd Ed., vol. 9, John Wiley & Sons, New York, 1980, p. 251–266), such as oxidation with m-chloroperbenzoic acid. Such an oxidation may also be performed on a styryl group.

In preferred embodiments of the fluorovinyl ethers of Formula I, p is 0, r is 1 and q is 1 to 10; or p is 1, r is 1 and q is 2. Preferred groups $R^1$ are: n-alkyl; $-(CH_2)_sR^3$ wherein s is 1 and $R^3$ is $-C\equiv CH$, $-CH=CH_2$, styryl, or

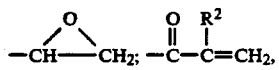

wherein $R^2$ is hydrogen or methyl; or $-(CH_2)_tR^5$ wherein t is 0 or 1. Especially preferred $R^1$ groups are $-(CH_2)_sR^3$, wherein s is 1 and $R^3$ is $-CH=CH_2$, styryl, or

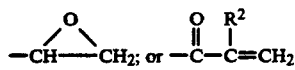

wherein $R^2$ is hydrogen or methyl. It is also preferred that when t is 0, the group $R^5$ be substituted with, or have substituents derived from, electron withdrawing groups, such as nitro or cyano. Amino, for example, is a substituent derived from an- electron withdrawing group, namely nitro. Also preferred are any and all combinations of the above preferred embodiments.

Preferred specific trifluorovinyl ethers are:

3,6,10-trioxa-5-trifluoromethyl-1,1,2,4,4,-5,7,7,8,8-decafluorohexadec-1-ene;

3,6,10-trioxa-5-trifluoromethyl-1,1,2,4,4,-5,7,7,8,8-decafluorooctacos-1-ene;

4,8,11-trioxa-9-trifluoromethyl-6,6,7,7,9,10,10,12,13,13-decafluorotridec-12-ene-1-yne;

3,6,10-trioxa-5-trifluoromethyl-1,1,2,4,4,5,7,7,8,8-decafluoro-11—(vinylphenyl)undec-1-ene; and 4,7-dioxa-5-trifluoromethyl-2,2,3,3,5,6,6,8,9,9-decafluoronon-8-enyl methacrylate.

The copolymer of trifluorovinyl ethers comprising units of the formula III

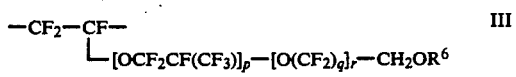

is made by the free radical copolymerization of the trifluorovinyl ethers described above with one or more other free radically polymerizable monomer. Free radical polymerization is a process well known to those skilled in the art, and may be carried out in solution, or for example, in water emulsion. If the latter is used, any functional groups in the trifluorovinyl ether should be stable to water. Initiators that are typically used for the free radical polymerization of fluoroolefins may be used, for example benzoyl peroxide, 4,4'-bis(t-butylcyclohexyl)peroxy dicarbonate, di-t-butyl peroxide, and a combination of ferrous ion and persulfate ion.

Copolymers with ethylene or vinyl monomers are preferred. Especially preferred comonomers are fluorinated vinyl monomers. More preferred monomers are vinylidene fluoride, tetrafluoroethylene, vinyl fluoride, perfluoro(methyl vinyl ether), chlorotrifluoroethylene, perfluoro-1-heptene, hexafluoropropylene and perfluoro-2,2-dimethyl-1,3-dioxole. The most preferred comonomer is tetra-fluoroethylene. In a copolymer containing a fluorinated vinyl monomer, it is preferred if the trifluorovinyl ether is about 20 mole percent or less of the total amount of monomer units in the polymer. It is believed that even this relatively small amount of the fluorinated vinyl ether will supply enough reactive groups (for example, epoxy) to crosslink the polymer, if desired, or, if $R^1$ is for example alkyl, change the surface properties of the polymer. Such surface properties include wettability and the ability to adhere various items to the polymer surface.

In preferred trifluorovinyl ether polymers, p is 0, r is 1 and q is 1 to 10; or p is 1, r is 1 and q is 2. Preferred groups $R^6$ are: n-alkyl; $-(CH_2)_sR^3$ wherein s is 1 and $R^3$ is $-C\equiv CH$, $-CH=CH_2$, or

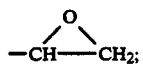

or $-(CH_2)_tR^5$ wherein t is 0 or 1. It is also preferred that when t is 0, the group $R^5$ be substituted with, or have substituents derived from, electron withdrawing groups, such as nitro or cyano. Also preferred are any and all combinations of the above preferred embodiments.

This invention includes homo- or copolymers made by the free radical polymerization of a compound of the formula IV

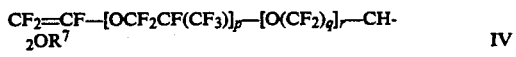

and optionally ethylene or vinyl monomers, wherein: $R^7$ is

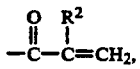

or —(CH$_2$)$_s$R$^4$;

R$^2$ is hydrogen or methyl;

R$^4$ is styryl;

p is an integer of 0 to 20;

q is an integer of 1 to 10;

r is 0 or 1; and s is 1, 2, 3 or 4;

provided that when r is 0, p is not 0. Such compounds are made by polymerization processes known to those skilled in the art. Thus the polymerization of these monomers is initiated by typical free radical initiators such as benzoyl peroxide, 4,4'-bis(t-butylcyclohexyl)peroxy dicarbonate, di-t-butyl peroxide, azobis(isobutyronitrile), or a combination of ferrous ion and persulfate ion. The polymerization may be carried out in solution, or may be done in emulsion.

Copolymers are formed with typical vinyl monomers, such as acrylic esters, acrylamides, styrene, vinyl acetate, propylene, tetrafluoroethylene, chlorotrifluoroethylene, vinyl fluoride, vinylidene fluoride, 4,7-dioxa-8,9-dichloro-5-trifluoromethyl-2,2,3,3,5,6,6,8,9,9-decafluoronona-1-ol, hexafluoropropylene, perfluoro-2,2-dimethyl-1,3-dioxole, and the like. Since the monomers of these polymers contain both an acrylic, styryl, acetylenic or olefinic functionality, as well as a trifluorovinyl ether, both of which may polymerize in free radical polymerizations, crosslinked polymers may result. It is believed, but Applicant does not wish to be bound, that the styryl or acrylic function is particularly easily polymerized. Again it is preferred if the trifluorovinyl ether containing monomer is about 20 mole percent or less of the total number of monomer units in the copolymer. This is sufficient for modification of the polymer surface properties and/or crosslinking of the polymer. Crosslinked polymers generally have better chemical resistance and retain their shape better at higher temperatures than uncrosslinked polymers. In this case, the polymer surface will be made hydrophobic by the presence of the trifluorovinyl ether group.

Preferred polymers are made from monomers where p is 0, r is 1 and q is 1 to 10; or p is 1, r is 1 and q is 2. In other preferred polymers, s is 1. Also preferred are any and all combinations of the above preferred embodiments.

The trifluorovinyl ethers of the instant invention are useful as monomers for the production of polymers. They are especially useful as comonomers with other monomers such as acrylic esters, styrene, propylene, tetrafluoroethylene, vinyl fluoride, vinylidene fluoride and hexafluoropropylene. Such polymers can be made by methods known to those skilled in the art. See the discussions herein, or for example, H. Mark, Ed., Encyclopedia of Polymer Science and Technology, John Wiley and Sons, New York, 1985, vol. 7, p. 256–269 and vol. 16, p. 577–644. The copolymers made from the trifluorovinyl ethers of the present invention and other monomers may be elastomers, thermoplastics or thermosetting resins, the latter two useful as molding resins. These copolymers, in particular copolymers of the trifluorovinyl ethers of the present invention with other fluorinated monomers, are useful for making chemically and heat resistant parts, and are useful in the oil, chemical and electronic industries.

The trifluorovinyl ether monomers of the present invention may also be used to change the surface properties of the copolymers in which they are incorporated, as for example to improve adhesion to nonfluorinated surfaces. Since many of them are reactive, they may also be used as crosslinking sites in elastomeric polymers, or as crosslinking sites in thermosetting polymers. The trifluorovinyl ethers may be used as comonomers with nonfluorinated monomers to produce polymers with different surface properties, for example, hydrophobicity. This is useful when water resistance is needed, as in coatings. The preparation and use of all such polymers is known to those skilled in the art, see for example H. Mark, supra.

The following abbreviations are used in the Examples:

Compound A—4,7-dioxa-8,9-dichloro-5-trifluoromethyl-2,2,3,3,5,6,6,8,9,9-decafluoronona-1-ol DMF—N,N-dimethylformamide NMR—nuclear magnetic resonance (spectroscopy)

TFE—tetrafluoroethylene

THF—tetrahydrofuran.

EXAMPLE 1

Preparation of Compound A

Methyl 4,7-dioxa-5-trifluoromethyl-2,2,3,3,5,6,6,8,9,9,-decafluoronon-8-enoate (600 g, 1.422 mole) was chlorinated with neat chlorine gas by bubbling the Cl$_2$ gas into it at 0°–5° C. The reaction was stopped when the conversion was almost complete. The resulting material was distilled to give the desired product as a clear, colorless liquid, yield 626 g (89.3%). Bp. 107° C./45 mm. H$^1$NMR (CDCl$_3$): δ3.96 (s).

The compound prepared above (98.6 g, 0.2 mole) was dissolved in absolute ethanol (60 ml) at 0° C. In a separate flask sodium borohydride (4.6 g, 0.12 mole) was mixed with absolute ethanol (80 ml) also at 0° C. The NaBH$_4$/EtOH solution was then added slowly into the other solution while being kept at <5° C. After the addition, the mixture was stirred at ambient temperature for 15 min, and then dumped into a mixture of 6N HCl (200 ml) and ice water (200 ml). The bottom layer was separated and the aqueous layer was extracted with ether. The organic layers were combined, washed with water repeatedly, and dried over magnesium sulfate. After the solvent was removed in vacuo, the residue was distilled to afford the desired compound as a clear, colorless liquid, yield 63 g (68%). Bp. 92°–93° C./25 mm. H$^1$NMR (CDCl$_3$): δ4.04 (t, J=14.1 Hz, 2H), 2.26 (s, br, 1H); F$^{19}$ NMR (CDCl$_3$): −71.3 (m, 2F), −77.4 (m, 1F), −80.3 (q, J=8.7 Hz, 3F), −82.4 to −86.0 (m, 4F), −126.7 (t, J=13.8 Hz, 2F), −146.2 (m, 1F).

EXAMPLE 2

Preparation of 3,6,10-Trioxa-1,2-dichloro-1,1,2,4,4,5,7,7,8,8-decafluoro-5-trifluoro-methyl-12,13-epoxytridecane NaH (2 g as 60% oil suspension, 0.05 mole) was suspended in THF solvent (25 ml) at 0° C. Compound A (23.3 g, 0.05 mole) in THF (5 ml) was added slowly and the pot was controlled at <10° C. After the addition, epibromohydrin (7 g, 0.051 mole) was introduced. Then the reaction was stirred at 40° C. for overnight, and the product was dumped into a mixture of ice-water (200 ml) and 6N HCl (30 ml). Ether was added to extract the organic product. The organic layer was washed with water, dried over MgSO$_4$, ether was removed in vacuo, and the residue was distilled to give the desired product as a clear liquid, yield 12 g (46%). Bp. 85° C./3.0 mm. H$^1$NMR (CDCl$_3$): δ3.98 (m, 3H), 3.52 (dd, J=12 Hz, 6 Hz, 1H), 3.17 (m, 1H), 2.83 (t, J=9 Hz, 1H), 2.62 (m, 1H); F$^{19}$NMR (CDCl$_3$): −71.2 (m, 2F), −77.4 (m, 1F), −80.2 (q, J=8.7 Hz, 3F), −82.4 to −85.9 (m, 4F), −123.8 (t, br, J=13.3 Hz, 2F), −146.2 (q, br, J=20.1 Hz, 1F).

EXAMPLE 3

Preparation of
3,6,10-Trioxa-1,2-dichloro-1,1,2,4,4,5,7,7,8,8-decafluoro-5-trifluoromethylhexadecane Compound A anion was prepared from Compound A (69.9 g, 0.15 mole) and NaH (6 g as 60% oil suspension, 0.15 mole) in DMF (180 ml)/THF (30 ml) mixed solvent as described in Example 2. To this solution was added 1-iodo-n-hexane (31.8 g, 0.15 mole)/THF (30 ml) solution, then the mixture was heated at 70° C. for 24 hrs. The reaction mixture was cooled and worked up as in Example 2 to give the title product as a clear, colorless liquid, yield 34.8 g (42.3% yield). Bp. 80° C./0.75 mm. H$^1$NMR (CDCl$_3$): δ3.85 (t, J=14 Hz, 2H), 3.58 (t, J=6.5 Hz, 2H), 1.60 (m, 2H), 1.32 (m, br, 6H), 0.92 (t, J=6.5 Hz, 3H); F$^{19}$NMR (CDCl$_3$): −71.2 (q, J=7 Hz, 2F), −77.3 (m, 1F), −80.2 (m, 3F), −82.2 to −85.8 (m, 4F), −123.6 (tm, J=14 Hz, 2F), −146.2 (q, J=20 Hz, 1F).

EXAMPLE 4

Preparation of
3,6,10-Trioxa-1,2-dichloro-1,1,2,4,4,5,7,7,8,8-decafluoro-5-trifluoromethyloctacosane This compound was prepared by the procedure of Example 2 from Compound A (23.3 g, 0.05 mole), NaH (2 g as 60% oil suspension, 0.05 mole) and C$_{18}$H$_{37}$I (18.2 g, 0.0478 mole) in THF (70 ml) in a similar procedure as described in Example 3. The desired compound was a clear, viscous liquid, yield 8.1 g (23.5%). Bp. 140° C./0.012 mm. H$^1$NMR (CDCl$_3$): δ3.85 (t, J=13.5 Hz, 2H), 3.56 (t, J=7.0 Hz, 2H), 1.57 (m, 2H), 1.27 (s, br, 30H), 0.89 (m, 3H); F$^{19}$NMR (CDCl$_3$): −71.2 (m, 2F), −77.4 (m, 1F), −80.2 (m, 3F), −82.5 to −86.0 (m, 4F), −123.6 (tm, J=13.4 Hz, 2F), −146.2 (q, br, J=21.1 Hz, 1F).

EXAMPLE 5

Preparation of
4,8,11-Trioxa-12,13-dichloro-6,6,7,7,9,10,10,12,13,13-decafluoro-9-trifluoromethyltridec-1-yne This compound was prepared by the procedure of Example 2 from Compound A (23.3 g, 0.05 mole), NaH (2 g as 60% oil suspension, 0.05 mole) and propargyl bromide (7.14 g, 0.06 mole) in DMF (60 ml)/THF (10 ml) mixed solvent. The desired compound was obtained as a clear liquid, yield 10.8 g (43%). Bp. 104° C./20 mm. H$^1$NMR (CDCl$_3$): δ4.30 (d, J=2.5 Hz, 2H), 4.00 (t, J=13.5 Hz, 2H), 2.52 (t, J=2.5 Hz, 1H); F$^{19}$NMR (CDCl$_3$): −71.2 (m, 2F), −77.4 (m, 1F), −80.2 (m, 3F), −82.4 to −86.0 (m, 4F), −123.4 (tt, J=1.7 Hz, 13.5 Hz, 2F), −146.2 (q, J=19.8 Hz, 1F).

EXAMPLE 6

Preparation of
3,6,10-Trioxa-1,2-dichloro-1,1,2,4,4,5,7,7,8,8-decafluoro-5-trifluoro-methyl-11-(vinylphenyl)undecane The title compound was prepared by the procedure of Example 2 from Compound A (23.3 g, 0.05 mole), NaH (2 g as 60% oil suspension, 0.05 mole) and vinyl benzylchloride (7.6 g, 0.05 mole, mixed isomers, purchased from Dow Chemical Co.) in DMF (65 ml)/THF (10 ml) mixed solvent at 80°–85° C. Workup and distillation afforded 19.7 g (68% yield) of the pale-yellow clear liquid. Bp. 95°–99° C./0.5 mm. H$^1$NMR (CDCl$_3$): δ7.42 to 7.20 (m, 4H), 6.62 (m, 1H), 5.75 (2s, 1H), 5.28 (2d, J=12 Hz, 1H), 4.64 (2s, 2H), 3.88 (2t, J=13.5 Hz, 2H); F$^{19}$NMR (CDCl$_3$): −71.2 (m, 2F), −77.4 (m, 1F), −80.2 (m, 3F), −82.4 to −86.0 (m, 4F), −123.3 (t, J=13.4 Hz, 2F), −146.2 (qm, J=18.8 Hz, 1F).

EXAMPLE 7

Preparation of
(3,6,10-Trioxa-1,2-dichloro-1,1,2,4,4,5,7,7,8,8-decafluoro-5-trifluoromethylnonyl) 2,4-Dinitrophenyl Ether This compound was made by the procedure of Example 2 from Compound A (46.5 g, 0.010 mole), NaH (4 g as 60% oil suspension, 0.10 mole) and 2,4-dinitrofluorobenzene (27.9 g, 0.15 mole) in THF (150 ml). The final product was purified by distillation to give a liquid product, yield 45.0 g (71.3%). Bp. 150°–160° C./0.5 mm. H$^1$NMR (CDCl$_3$): δ8.80 (d, J=2.5 Hz, 1H), 8.70 (dd, J=2.5, 10 Hz, 1H), 7.24 (d, J=10 Hz, 1H), 4.68 (t, J=12 Hz, 2H); F$^{19}$NMR (CDCl$_3$): −71.3 (d, J=10.1 Hz, 2F), −77.4 (m, 1F), −80.2 (q, J=7.6 Hz, 3F), −82.5 to −86.0 (m, 4F), −122.9 (t, J=11.6 Hz, 2F), −145.9 (q, J=19.4 Hz, 1F).

EXAMPLE 8

Preparation of
(3,6,10-Trioxa-1,2-dichloro-1,1,2,4,4,5,7,7,8,8-decafluoro-5-trifluoromethylnonyl) 2,4-Diaminophenyl Ether The dinitro compound obtained from Example 7 (22.1 g, 0.035 mole) was mixed with 10% Pd/C (2.2 g) in ethyl acetate/ethanol (6/4 by volume, 88 g) solvent. Hydrogenation was carried out with 50–60 psi of hydrogen pressure at ambient temperature for about 6 hrs. After reaction, the solution was filtered to remove the metal residue and the solvent was removed in vacuo. The final diamino product was purified by distillation, 4.75 g of (24% yield) clear, viscous liquid was obtained. Bp. 120° C./0.02 mm. H$^1$NMR (CDCl$_3$): δ7.61 (d, J=8.0 Hz, 1H), 6.08 (d, J=2.0 Hz, 1H), 6.02 (dd, J=2 Hz, 8 Hz, 1H), 4.11 (t, J=13.5 Hz, 2H), 3.55 (s, br, 4H, —NH$_2$); F$^{19}$NMR (CDCl$_3$): −71.3 (m, 2F), −77.5 (m, 1F), −80.2 (m, 3F), −82.3 to −86.0 (m, 4F), −124.0 (m, 2F), −146.2 (m, 1F).

EXAMPLE 9

Preparation of
3,6,10-Trioxa-5-trifluoromethyl-1,1,2,4,4,5,7,7,8,8-decafluorohexadec-1-ene Zinc dust (7.80 g, 0.12 mole) in DMF (60 ml) solvent was activated with bromine (0.1 ml) and was heated at 90°–95° C. The substrate obtained from Example 3 (32.96 g, 0.06 mole) was added and the reaction proceeded for 24 hrs. After cooling, ether was added to extract the product. The ether layer was washed with water, and dried over magnesium sulfate. The residue was distilled after ether solvent was removed in vacuo, to give 23.2 g (81% yield) of the desired product as a clear, colorless liquid. Bp. 75° C./3 mm. H$^1$NMR (CDCl$_3$): δ3.86 (t, J=13.5 Hz, 2H), 3.55 (t, J=6.6 Hz, 2H), 1.60 (m, 2H), 1.33 (m, br, 6H), 0.88 (t, J=6.5 Hz, 3H); F$^{19}$NMR (CDCl$_3$): −80.3 (t, J=4.7 Hz, 3F), −84.1 (m, br, 2F), −85.2 (m, br, 2F), −123.6 (t, J=13.5 Hz, 2F), −145.8 (t, J=21.8 Hz, 1F), −113.5, −113.8, −113.9, −114.3 (4s, 1F), −121.6, −122.1, −122.2, −122.7 (4t, J=5.3 Hz, 1F), −135.2, −135.6, −135.8, −136.2 (4t, J=5.7 Hz, 1F).

EXAMPLE 10

Preparation of
3,6,10-Trioxa-5-trifluoromethyl-1,1,2,4,4,5,7,7,8,8-decafluorooctacos-1-ene This compound was prepared from the product of Example 4 and zinc dust (1.64 g, 0.025 mole) in DMF solvent (12 ml) as described in Example 9. After workup, the desired product 3.42 g (48.1% yield) was obtained as a pale-yellow liquid. Bp. 135° C./0.02 mm. H$^1$NMR (CDCl$_3$): δ3.86 (t, J=13.5 Hz, 2H), 3.55 (t, J=7.2 Hz, 2H), 1.57 (m, 2H, 1.28 (s, br, 30H), 0.88 (m, 3H); F$^{19}$NMR (CDCl$_3$): −80.4 (m, 3F), −84.2 (m, 2F), −85.3 (m, 2F), −123.6 (t, J=13.5 Hz, 2F), −145.8 (t, J=21.3 Hz, 1F), −113.5, −113.9, −114.0, −114.3 (4s, 1F), −121.7, −122.1, −122.3, −122.7 (4t, J=5.2 Hz, 1F), −135.2, −135.6, −135.8, −136.1 (4t, J=5.7 Hz, 1F).

EXAMPLE 11

Preparation of
4,8,11-Trioxa-9-trifluoromethyl-6,6,7,7,9,10,10,12,13,13-decafluorotridec-12-ene-1-yne The title compound was prepared from 10.1 g, 0.02 mole of the product of Example 5 and zinc dust (2.6 g, 0.04 mole) in DMF solvent (20 ml) as described in Example 9. The desired product was obtained as a clear, colorless liquid, yield 6.74 g (78%). Bp. 100° C./65 mm. H$^1$NMR (CDCl$_3$): δ4.30 (d, J=2.5 Hz, 2H), 4.00 (t, J=13.5 Hz, 2H), 2.51 (t, J=2.5 Hz, 1H); F$^{19}$NMR (CDCl$_3$): −80.3 (s, br, 3F), −84.2 (s, br, 2F), −85.3 (m, br, 2F), −123.3 (t, J=13.3 Hz, 2F), −145.7 (t, J=21.8 Hz, 1F), −113.4, −113.7, −113.8, −114.2 (4s, 1F), −121.6, −122.0, −122.2, −122.6 (4t, J=5.1 Hz, 1F), −135.2, −135.6, −135.8, −136.2 (4t, J=5.7 Hz, 1F).

EXAMPLE 12

Preparation of
3,6,10-Trioxa-5-trifluoromethyl-1,1,2,4,4,5,7,7,8,8-decafluoro-11-(vinylphenyl)undec-1-ene This compound was made from 11.62 g, 0.02 mole, of the product of Example 6 and zinc dust (2.6 g, 0.04 mole) in DMF solvent (20 ml). After the same workup procedure as Example 9, the desired compound 4.37 g (43% yield) was obtained as a pale-yellow liquid. Bp. 85° C./0.9 mm. H$^1$NMR (CDCl$_3$): δ7.48 to 7.20 (m, 4H), 6.72 (m, 1H), 5.76 (2s, 1H), 5.27 (2d, J=10.8 Hz, 1H), 4.63 (2s, 2H), 3.88 (2t, J=13.5 Hz, 2H); F$^{19}$NMR (CDCl$_3$): −80.3 (m, 3F), −84.2 (m, 2F), −85.2 (m, 2F), −123.2 (t, J=13.4 Hz, 2F), −145.7 (t, J=21.8 Hz, 1F), −113.3, −113.7, −113.8, −114.1 (4s, 1F), −121.5, 122.0, −122.1, −122.6 (4t, J=5.4 Hz, 1F), −135.2, −135.5, −135.8, −136.1 (4t, J=5.7 Hz, 1F).

EXAMPLE 13

Preparation of
4,7-Dioxa-5-trifluoromethyl-2,2,3,3,5,6,6,8,9,9-decafluoronon-8-enyl Methacrylate To dry flask charged methyl 4,7-dioxa-5-trifluoromethyl-2,2,3,3,5,6,8,9,9-decafluoronon-8-enoate (211 g, 0.50 mole) in absolute ethanol (300 ml) with a magnetic stirring bar. Sodium borohydride (11.34 g, 0.30 mole) was added slowly from a solid addition funnel. The reaction was somewhat exothermic and the reaction pot was kept at ≦10° C. by external cooling. After the addition of sodium borohydride was completed, the reaction mixture was stirred for 1 hr at room temperature. The pot mixture was then dumped into an ice water (600 ml)/6N HCl (600 ml) mixture. The bottom product layer was separated, washed with water and distilled to give the corresponding alcohol as a clear, colorless liquid. Bp. 68° C./25 mmHg. Yield: 168.7 g (85.6%).

The alcohol was dissolved in methylene chloride at 0°-5° C. in the presence of pyridine (5.93 g, 0.075 mole). Methacrylyl chloride (8.7 g, 90% purity, 0.075 mole, purchased from Aldrich Chemical Co.) was added slowly, and the mixture was allowed to stir 1 hr at 5° C. after the addition. The mixture was then dumped into ice water, the bottom organic layer was separated, washed with 5% HCl and water, and dried over magnesium sulfate. The solvent was removed in vacuo, and the residue was distilled to give the desired product as a clear, colorless liquid, yield 17.3 g (74.8%). Bp. 75° C./5 mm. H$^1$NMR (CDCl$_3$): δ6.21, 6.24 (2s, br, 1H), 5.70, 5.82 (2s, br, 1H), 4.59 (t, J=13.5 Hz, 2H), 1.98, 2.02 (2s, br, 3H); F$^{19}$NMR (CDCl$_3$): −80.4 (m, 3F), −84.3 (m, 2F), −85.3 (m, 2F), −123.4 (t, J=13.0 Hz, 2F), −145.8 (t, J=21.6 Hz, 1F), −113.3, −113.6, −113.7, −114.1 (4s, 1F), −121.5, −121.9, −122.1, −122.5 (4t, J=5.6 Hz, 1F), −135.3, −135.6, −135.9, −136.2 (4t, J=5.8 Hz, 1F).

EXAMPLE 14

Free Radical Copolymerization of Tetrafluoroethylene and
3,6,10-Trioxa-5-trifluoromethyl-1,1,2,4,4,5,7,7,8,8-decafluorohexadec-1-ene The monomer (2 g) prepared as described in Example 9 was dissolved in 1,1,2-trichloro-1,2,2-trifluoroethane (10 g) in the presence of 4,4'-bis(t-butylcyclohexyl)-peroxy dicarbonate initiator (0.01 g) in a 75 ml stainless steel tube. This tube was pressurized with tetrafluoroethylene to 40 psi at room temperature. The tube was then sealed and was heated at 50° C., 70° C. and 90° C. for 2 hrs each respectively. Solvent was removed from the resulting polymer which was then washed with water, acetone and ether, dried under vacuum (150 mm) at 100° C. for 24 hrs. White polymer (3.3 g) was obtained, which had a Tg at 180° C. and two Tm's at 258 and 320° C. respectively. The composition of this polymer was TFE/CF$_2$=CFOCF$_2$CF(CF$_3$)O—CF$_2$CF$_2$C-H$_2$O—C$_6$H$_{13}$=93.6/6.4 (mole %) by F$^{19}$ high temperature NMR spectroscopy.

EXAMPLE 15

Free Radical Homopolymerization of 4,7-Dioxa-5-trifluoromethyl-2,3,3,5,6,6,8,9,9-decafluoronon-8-enyl Methacrylate The title monomer (3.0 g) and benzoyl peroxide (0.01 g) were sealed in a vial with a stirrer under an inert atmosphere. The polymerization proceeded at 65° C. for 70 hrs, then at 100° C. for 8 hrs. At this time a tough, transparent and white solid polymer was obtained in quantitative yield.

EXAMPLE 16

Free Radical Homopolymerization of 3,6,10-Trioxa-5-trifluoromethyl-1,1,2,4,4,5,7,7,8,8-decafluoro-11-(vinylphenyl)undec-1-ene The title monomer (2.0 g) and benzoyl peroxide (0.01 g) were sealed in a reaction vial. The polymerization was carried out at 65° C. for 70 hrs. A hard polymer, 1.92 g, was obtained after washing and drying. This polymer had good resistance toward common organic solvents, such as acetone, chloroform, THF, etc.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A trifluorovinyl ether of the formula

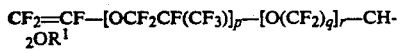

wherein:
$R^1$ is alkyl or cycloalkyl containing 1 to 30 carbon atoms,

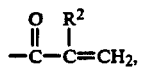

$-(CH_2)_sR^3$ or $-(CH_2)_tR^5$;
$R^2$ is hydrogen or methyl;
$R^3$ is $-C\equiv CH$, $-CH=CH_2$, styryl, or

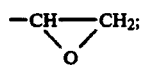

$R^5$ is aryl or substituted aryl;
p is an integer of 0 to 20;
q is an integer of 1 to 10;
r is 0 or 1;
s is 1, 2, 3 or 4; and
t is 0, 1, 2, 3 or 4;
provided that when r is 0, p is not 0.

2. The trifluorovinyl ether of claim 1 wherein said p is 0, said r is 1, and said q is 1 to 10.

3. The trifluorovinyl ether of claim 1 wherein said p is 1, said r is 1, and said q is 2.

4. The trifluorovinyl ether of claim 1 wherein said $R^1$ group is:
n-alkyl;
$-(CH_2)_sR^3$ wherein s is 1, and $R^3$ is $-C\equiv CH$, $-CH=CH_2$, styryl, or

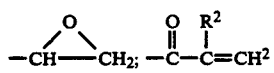

wherein $R^2$ is hydrogen or methyl; or $-(CH_2)_tR^5$ wherein t is 0 or 1.

5. The trifluorovinyl ether of claim 4 wherein said $R^1$ group is $-(CH_2)_sR^3$ wherein s is 1 and $R^3$ is styryl, $-CH=CH_2$ or

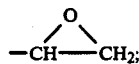

said $R^1$ group is

wherein $R^2$ is hydrogen or methyl.

6. The trifluorovinyl ether of claim 1 wherein said t is 0, and said substituted aryl is substituted with, or has substituents derived from, electron withdrawing groups.

7. The trifluorovinyl ether of claim 4 wherein said p is 0, said r is 1, and said q is 2.

8. The trifluorovinyl ether of claim 4 wherein said p is 1, said r is 1 and said q is 2.

9. The trifluorovinyl ether of claim 1 which is:

3,6,10-trioxa-5-trifluoromethyl-1,1,2,4,4,5,7,7,8,8-decafluorohexadec-1-ene;
3,6,10-trioxa-5-trifluoromethyl-1,1,2,4,4,5,7,7,8,8-decafluorooctacos-1-ene;
4,8,11-trioxa-9-trifluoromethyl-6,6,7,7,9,10,10,12,13,13-decafluorotridec-12-ene-1-yne;
3,6,10-trioxa-5-trifluoromethyl-1,1,2,4,4,5,7,7,8,8-decafluoro-11-(vinylphenyl)undec-1-ene; or
4,7-dioxa-5-trifluoromethyl-2,2,3,3,5,6,6,8,9,9-decafluoronon-8-enyl methacrylate.

* * * * *